United States Patent [19]
Watkins et al.

[11] Patent Number: 5,911,695
[45] Date of Patent: Jun. 15, 1999

[54] SHOULDER TESTER

[75] Inventors: K. Richard Watkins; Raymond A. Sachs, both of San Diego, Calif.

[73] Assignee: Medmetric Corporation, San Diego, Calif.

[21] Appl. No.: 08/963,404

[22] Filed: Nov. 3, 1997

[51] Int. Cl.⁶ .................................................. A61B 5/103
[52] U.S. Cl. .......................................... 600/587; 600/553
[58] Field of Search .................................. 600/587, 598, 600/594, 553

[56] References Cited

U.S. PATENT DOCUMENTS

| | | |
|---|---|---|
| 2,716,978 | 9/1955 | Torricelli .................................. 600/553 |
| 3,285,070 | 11/1966 | McDonough . |
| 3,374,675 | 3/1968 | Keropian . |
| 3,420,222 | 1/1969 | Noe . |
| 3,680,386 | 8/1972 | Cannon . |
| 4,220,163 | 9/1980 | Malek Afzali . |
| 4,294,015 | 10/1981 | Drouin et al. . |
| 4,374,588 | 2/1983 | Ruggles . |
| 4,534,364 | 8/1985 | Lamoreux .................................. 600/587 |
| 4,549,555 | 10/1985 | Fraser et al. . |
| 4,571,834 | 2/1986 | Fraser et al. . |
| 4,583,554 | 4/1986 | Mittelman et al. . |
| 4,583,555 | 4/1986 | Malcom et al. . |
| 4,799,497 | 1/1989 | Riley, II . |
| 4,823,807 | 4/1989 | Russell et al. . |
| 4,834,057 | 5/1989 | McLeod, Jr. . |
| 4,909,262 | 3/1990 | Halpern et al. .......................... 600/587 |
| 4,969,471 | 11/1990 | Daniel et al. ............................ 600/587 |
| 5,116,296 | 5/1992 | Watkins et al. . |
| 5,156,163 | 10/1992 | Watkins et al. . |
| 5,179,939 | 1/1993 | Donovan et al. . |
| 5,662,121 | 9/1997 | Zucker et al. .......................... 600/587 |

Primary Examiner—Cary O'Connor
Assistant Examiner—Pamela L. Wingood
Attorney, Agent, or Firm—Nydegger & Associates

[57] ABSTRACT

A device for testing a shoulder of a patient includes a base with a pivot arm extending therefrom. A force indicator is located at the extended end of the arm and a movement indicator is mounted on the device at its base. In order to prepare for the operation of the device, the patient is placed to effectively hold the shoulder stationary. The base of the device is then positioned on the clavicle and the force indicator is positioned on the humeral head. Preferably, the force indicator is secured to the shoulder with a strap. To test the shoulder once the device is properly positioned on the patient, a force is applied to the force indicator. This applied force is transferred directly to the humeral head and the results of its application are recorded. Specifically, the magnitude of the applied force is measured by the force indicator and the movement of the humeral head relative to the clavicle is measured by the movement indicator. The recorded measurements are then used for diagnostic purposes.

17 Claims, 3 Drawing Sheets

SHOULDER TESTER

FIELD OF THE INVENTION

The present invention pertains generally to equipment which is useful for making measurements of anatomical movements for diagnostic purposes. More specifically, the present invention pertains to diagnostic equipment which measures anatomical movements in response to the application of measured forces. The present invention is particularly, but not exclusively useful, as a device for testing the inferior glenohumeral ligament in the shoulder of a patient with the application of a measurable force.

BACKGROUND OF THE INVENTION

A well known and widely used procedure for diagnosing damage to the ligaments and muscles of an anatomical joint in the skeletal structure of the body has been to apply forces against the body and observe the resultant response. The premise is that upon application of a properly applied force to the body structure, several factors can be observed to form the basis for a valid diagnosis. These factors include: 1) the resistance encountered; 2) the extent of relative bone movement; and 3) the nature of the resultant joint movement. Heretofore, however, the procedures which have been used are somewhat unreliable and inconclusive. In most instances the force has been applied by simple manipulation of the suspected joint. Importantly, this manipulation has been without knowledge of the exact magnitude of the applied force and without certainty as to the direction of the force or the point at which the force has been applied. Consequently, conclusions have been subjectively ascertained. As such, they are based on inconsistencies and subject to question.

It is clear that more accurate conclusions about the health of joint ligaments and muscles could be made if the testing procedures were more standardized and more accurately performed. For the type of testing envisioned by the present invention this requires that the magnitude and direction of the applied force, as well as its point of application, all be accurately determined. Further, once the force application is accurately quantified, the extent of any resultant movement in the anatomical structure of the body needs to be accurately measured. To do this is not a simple matter. Certainly it is not a procedure which can be repetitively duplicated with consistency by simple manipulation. The consequence has been a growing recognition that mechanical devices and apparatus can be used to obtain the consistency and accuracy that is otherwise elusive.

As is well known, the body has many joints, and all are anatomically different. Not only will the set up for applying a force against a joint be different, the various joints will themselves react differently to the applied force. Consequently, each joint should be considered separately, on its own. With this in mind, consider the knee. An example of a device which has been specifically designed and engineered to assist the physician in diagnosing the health of ligaments and muscles in a knee joint is the device which is claimed and disclosed in U.S. Pat. No. 4,969,471 (hereinafter the '471 patent). The '471 patent which issued to Daniel et al. for an invention entitled "Knee Ligament Testing Device and Method of Use" is assigned to the assignee of the present invention. Unlike the device disclosed in the '471 patent, however, the present invention is concerned with the shoulder.

The ligaments and muscles of the shoulder can be tested by examining the movement and displacement of the humeral head relative to the scapulae and clavicle. To do this, it is preferable if both the clavicle and the scapular spine can be held stationary. Once the clavicle and scapular spine have been fixed and are held in place, a force is then applied to the humeral head to move the humeral head. As indicated above, with knowledge of the exact magnitude of the applied force, and with certainty as the direction in which the force is applied against the humeral head, a measurement of humeral head movement and displacement relative to the scapulae and clavicle will provide a valid basis for diagnosing the health of the ligaments and muscles in the shoulder. Of particular concern is the inferior glenohumeral ligament.

It is known anatomically that both static and dynamic stabilizers serve to reduce potential humeral displacement relative to the scapulae and clavicle. The static stabilizing elements include the glenohumeral ligaments, and the dynamic stabilizers include the overlying rotator cuff. There are three glenohumeral ligaments (superior, middle and inferior) which are formed by localized condensations of the joint capsule fibers and which are the primary static stabilizers when taut. Of these, the inferior glenohumeral ligament is the largest and is thought to play the greatest role in prevention of dislocation.

It happens that the glenohumeral joint is most prone to traumatic subluxation or dislocation when the arm is in the abducted and externally rotated position. In this position, the inferior glenohumeral ligament, which is lax in adduction, becomes taut. Indeed, the inferior glenohumeral ligament gradually tightens as abduction increases such that at 90 degrees it acts as the primary restraint to anterior displacement. With this in mind, any insufficiencies in the inferior glenohumeral ligament can be revealed with proper testing.

In addition to testing the inferior glenohumeral ligaments, as the target structure, an increased capability for testing the shoulder at varying angles will perhaps prove useful in testing secondary restraints. Further, where the subject injury is acute or where pain limits rotation testing to positions other than the preferred position, testing may still be necessary and may still prove diagnostic.

In light of the above it is an object of the present invention to provide an apparatus for testing the shoulder of a patient which can be repetitively used to obtain consistent results. Another object of the present invention is to provide a shoulder tester which will test shoulders with the arm at any angle, (0 to 90 deg.), with the subject sitting or supine, with the arm adducted, abducted or otherwise. It is another object of the present invention to provide an apparatus for testing the shoulder of a patient which accurately directs a force against the humeral head. Yet another object of the present invention is to provide an apparatus for testing the shoulder of a patient which simultaneously measures the magnitude of a force applied against the humeral head and the extent of the resultant movement of the humeral relative to the clavicle. Still another object of the present invention is to provide an apparatus for testing the shoulder of a patient which is simple to use, relatively easy to manufacture and comparatively cost effective.

SUMMARY OF THE PREFERRED EMBODIMENTS

An apparatus for testing the shoulder of a patient to determine the health of ligaments and muscles of the shoulder includes a base which has an extension arm that interconnects the base with a force indicator housing. A swivel plate is mounted on the base and is configured to substantially conform with the patient's clavicle. As intended for the present invention, the swivel plate is allowed to swivel or rotate such that it can be placed against either the patient's left or right clavicle, depending on which shoulder is to be tested.

A pressure plate is slidingly mounted on the force indicator housing, and a spring is positioned between the pressure plate and the housing for compression or extension in response to movement of the pressure plate on the housing. Preferably, this spring has a known spring constant and has a linear response over the operational range of the pressure plate. Additionally, a handle can be attached to the force indicator housing, and a securing strap can be connected either to the housing or to the pressure plate.

An elongated pivot arm extends separately from the base of the apparatus along with the extension arm. More specifically, the pivot arm has one end which is pivotally mounted for rotation on the base and it has a free end which is positioned in the force indicator housing for movement on an arc around the pivot point of the pivot arm on the base. Further, a movement indicator, such as a Hall-effect device, is mounted on the base to measure any rotational movement of the pivot arm.

Inside the force indicator housing, a post is connected with the free end of the pivot arm. This post, however, is not directly connected with either the force indicator housing or the pressure plate. Thus, the post is free to move with the free end of the pivot arm. Importantly, the post is oriented in the force indicator housing so it can be referenced with the pressure plate. While maintaining reference with the pressure plate, the post is free for subsequent movement with the pressure plate relative to the housing.

Electronic computer and display components which are mounted on the base of the apparatus are connected with both the force indicator and the movement indicator. These components simultaneously record the application of a force against the patient by the pressure plate, and the movement of the patient and pressure plate in response to this force. Specifically, connections between the electronic components and the Hall-effect device of the movement indicator record movement of the pressure plate. Similarly, connections between the electronic components and the spring record the magnitude of the force that is being applied. Proper initial positioning of the apparatus on the patient establishes the direction of the force against the patient.

In the operation of the apparatus of the present invention, the patient may be either sitting or supine. Preferably, the patient is first placed on a flat, and preferably hard, surface with his/her scapular spine positioned against the surface. Regardless of patient position, however, the swivel plate is then positioned against the patient's clavicle and the pressure plate of the force indicator is positioned against the humeral head. The strap is then wrapped around the shoulder of the patient and secured to hold the apparatus on the patient. The arm of the patient can be at any angle.

With the apparatus in place on the patient, and with the base of the apparatus held stationary on the clavicle of the patient, the operator pushes down on the handle. This action exerts a force against the patient which moves the humeral head of the patient's shoulder. Importantly for the present invention, as this force is applied, several consequences result. For one, in response to the force, the spring compresses between the pressure plate and the force indicator housing. Due to the linearity of the spring constant, the change in length of the spring is indicative of the magnitude of the applied force. This information is conveyed to the electronic equipment for display. For another, the force on the handle is transferred through the pressure plate of the apparatus to the humeral head. Depending on the health of the shoulder, this causes the humeral head to move and displace relative to the scapulae and clavicle. As the humeral head moves, so does the pressure plate which is being pushed against the humeral head. Consequently, the post also moves. Importantly, as the post moves with the pressure plate, the post causes the pivot arm to rotate. This rotation is then sensed by the Hall-effect device, and a consequent signal, indicative of humeral head movement, is conveyed to the electronic components for display. Thus, with the direction and location of the applied force known (due to proper positioning of the apparatus on the patient), with the magnitude of the applied force known (determined by the force indicator of the apparatus), and with the resulting extent of humeral head movement known (determined by the movement indicator of the apparatus), a valid assessment of the health of ligaments and muscles in the shoulder can be made.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
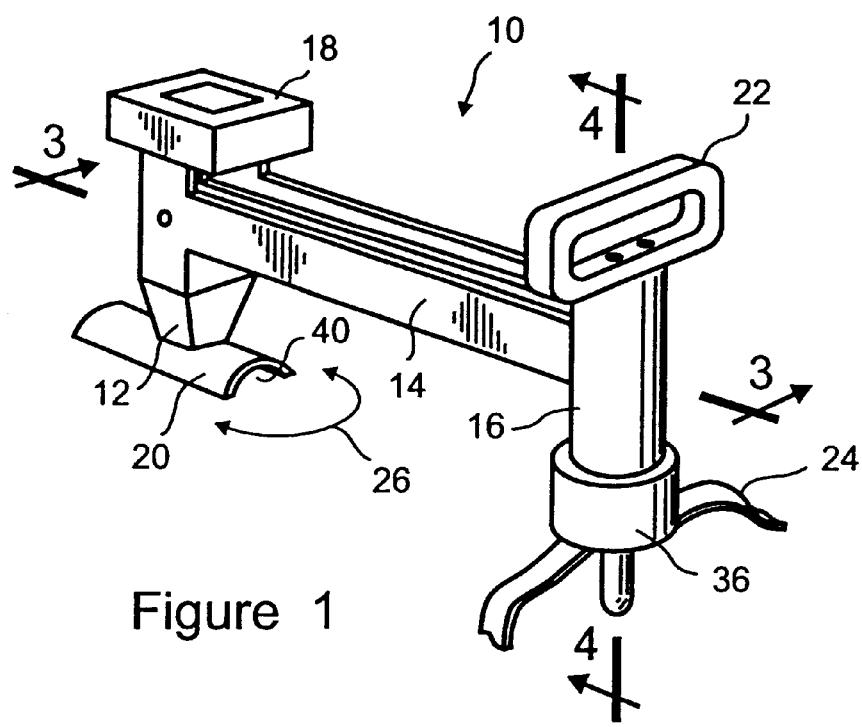
FIG. 1 is a perspective view of the device of the present invention.

Referring initially to FIG. 1, an apparatus in accordance with the present invention is shown and generally designated 10. As shown in FIG. 1, the apparatus 10 includes a base 12, an extension arm 14 which interconnects the base 12 with a housing 16, and a display 18 which is mounted on the base 12. FIG. 1 also shows that a swivel plate 20 is mounted on the base 12, and that a handle 22 and a strap or clamp 24 are attached to the housing 16.

Preferably, the swivel plate 20 is mounted for rotation on the base 12 so that it can swivel, or swing, back and forth in the directions indicated by arrows 26. Movement of the swivel plate 20 is in free rotation on the apparatus 10 and, as will be made clear with subsequent disclosure, this movement is necessary in order to properly conform the apparatus 10 for its operation.

Figure 2:
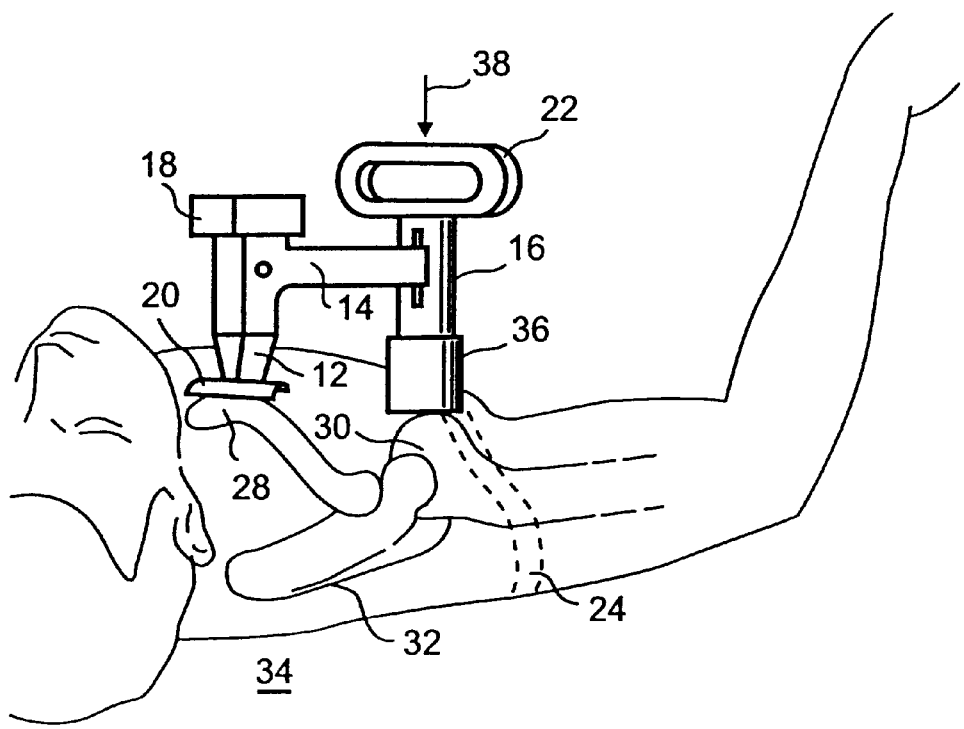
FIG. 2 is a view of the device of the present invention positioned on the shoulder of a patient, with portions of the patient's skeletal structure shown for clarity.

As shown in FIG. 2, the apparatus 10 is positioned on a patient for its operation. In order to illustrate the proper placement of apparatus 10 on the patient, the interior skeletal structure of the patient's shoulder has been exposed in FIG. 2. Specifically shown are the clavicle 28, the humeral head 30 and the scapular spine 32. With the patient reclined on a hard surface 34, it will be appreciated that the scapular spine 32 will generally rest on this surface 34 and, thus, be supported by the surface 34. As indicated above, however, the patient may be sitting and the arm of the patient may be at any angle so long as the clavicle 28 and scapular spine 32 can be stabilized as pressure is applied to the humeral head 30.

To properly position the apparatus 10 on the patient, the swivel plate 20 is positioned against the clavicle 28. The extension arm 14 is then rotated to position the housing 16 against the humeral head 30. More specifically, a pressure plate 36 which is slidingly mounted on the housing 16 is positioned against the humeral head 30. Next the strap 24, or any suitable attachment means, such as a clamp or similar restraint, is passed around the shoulder of the patient and secured to hold the pressure plate 36 against the humeral head 30. The apparatus 10 can then be used as intended. This includes exerting a force downward on the handle 22, substantially in the direction of arrow 38, and observing the measurements presented on the display 18. The actual operation of apparatus 10 will be best appreciated by reference to FIGS. 3 and 4.

Figure 3:
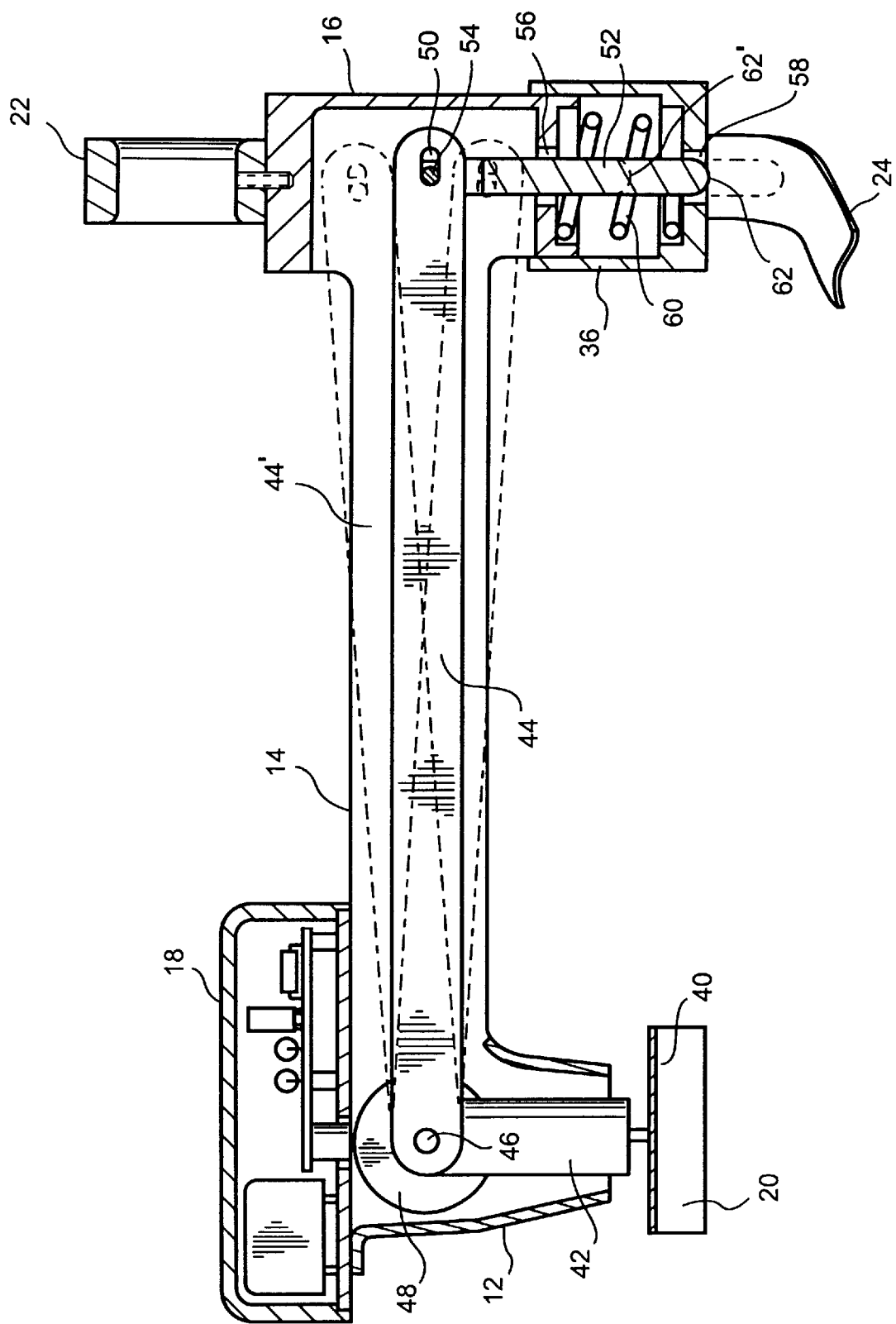
FIG. 3 is a cross-sectional view of the device as seen along the line 3—3 in FIG. 1.
Figure 4:
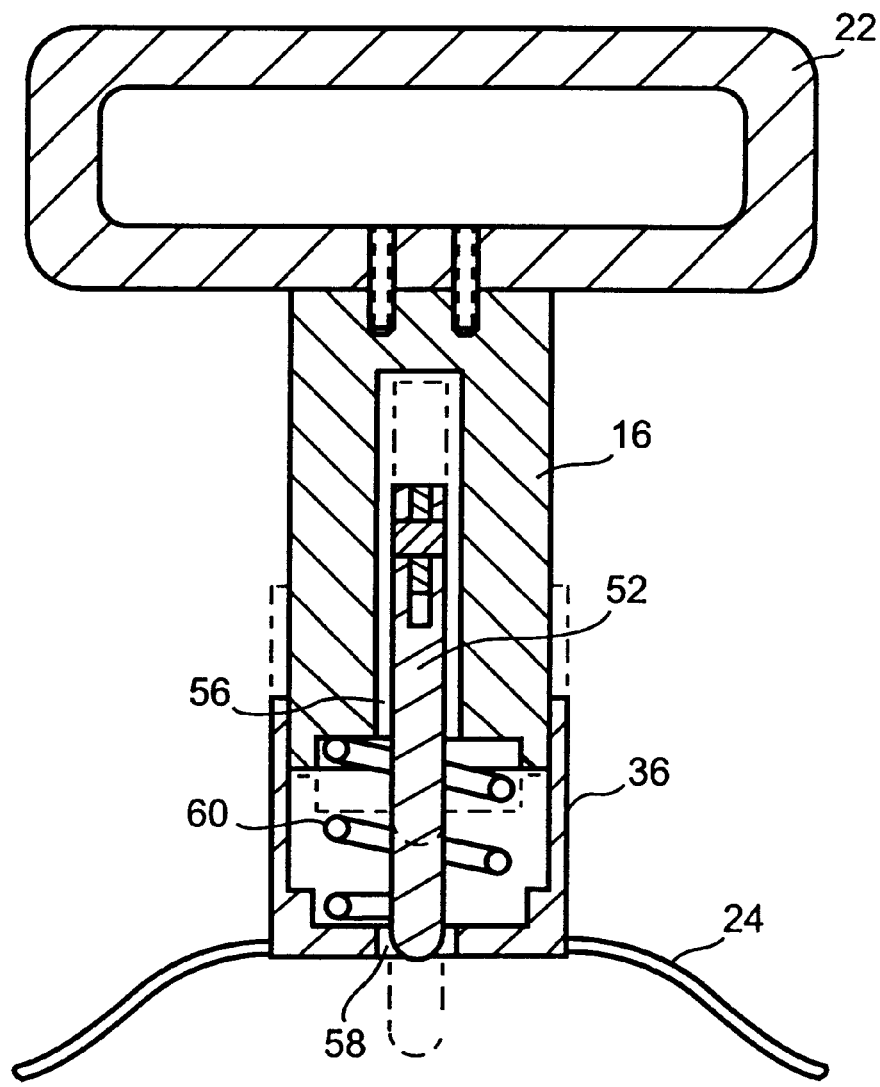
FIG. 4 is a cross-sectional view of the device as seen along the line 4—4 in FIG. 1.

In FIG. 3 it will be seen that the swivel plate 20 is formed with a channel 40. As indicated above, and demonstrated in FIG. 2, this channel 40 allows the swivel plate to generally conform with the clavicle 28 when the apparatus 10 is positioned on the patient. The swivel plate 20 is mounted for rotation on a base member 42. Also mounted on the base member 42 is a pivot arm 44. Specifically, the pivot arm 44 is attached to the base member 42 by a pin 46 which establishes the point about which the pivot arm 44 rotates. Additionally, a movement indicator 48 is attached to the pivot arm 44 to indicate any rotational movement of the pivot arm 44. Preferably, the movement indicator 48 is of a type well known in the art, such as a Hall-effect device.

While one end of the pivot arm 44 is attached to the base member 42 for rotation about the pin 46, the other end of the pivot arm 44 is unconstrained. Thus, it is substantially free for some, albeit limited, movement on an arc in rotation about the pin 46. As shown, the free end of pivot arm 44 is positioned inside the housing 16 of the force indicator and is formed with an elongated key way 50 which is longitudinally oriented on the pivot arm 44. Apparatus 10 also has a post 52 which is located in the housing 16. This post 52 includes a pin 54 that is inserted into the key way 50 of pivot arm 44 so that the pivot arm 44 and post 52 will move in concert with each other. Further, the post 52 is constrained to linear movement by a slot 56 in housing 16 and a slot 58 in pressure plate 36. Thus, as the free end of pivot arm 44 moves along its arc, the post 52 follows with a linear movement in the housing 16, or vice versa. Perhaps, the movement of post 52 can best be appreciated by cross referencing FIGS. 3 and 4.

FIG. 3 also shows that a spring 60 is mounted between the housing 16 and the pressure plate 36. Specifically, as indicated above, the pressure plate 36 is slidingly disposed on the housing 16. Thus, the spring 60 will compress or extend according to the relative movement between pressure plate 36 and housing 16. By using a spring 60 which has a spring constant that gives a substantially linear response over the operational range of movement for spring 60, the relative movement between pressure plate 36 and housing 16 can be used to determine the magnitude of the force that is being applied by apparatus 10 against the humeral head 30.

In the operation of apparatus 10, the apparatus 10 is first positioned on the patient. To do this the patient is positioned with his/her scapular spine 32 resting against a surface 34. Then, the swivel plate 20 of apparatus 10 is positioned over and against the clavicle 28. Pressure plate 36 is then positioned over and against the humeral head 30. Note that with the placement of the pressure plate 36 on humeral head 30, the post 52 will be moved so that the exposed end 62 of the post 52 is flush with the pressure plate 36. This movement references the post 52 so that the post 52 will thereafter move along with the pressure plate 36 as the pressure plate 36 moves relative to the housing 16.

Once the apparatus 10 is properly positioned on the patient, the base 12 of apparatus 10 is held stationary relative to the clavicle 28. A force is then applied to the handle 22. In response to this applied force, the humeral head 30 will exert an equal but opposite reactive force against the pressure plate 36. Due to this reactive force, the pressure plate 36 will move on housing 16 and compress spring 60. Additionally, the post 52 will move with pressure plate 36 and rotate pivot arm 44. With the movement of pressure plate 36, the magnitude of the applied force can be ascertained by well known methods and presented on display 18. With the movement of the post 52 and pivot arm 44, the extent of movement of the humeral head 30 relative to the clavicle 28 can be ascertained by well known methods and presented on display 18. The operator then uses the measurements shown on display 18 as a basis for diagnosing the health of the ligaments and muscles in the patient's shoulder.

While the particular apparatus for testing a shoulder of a patient as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for testing a shoulder of a patient which comprises:

a base configured to be stationarily juxtaposed on the clavicle of the shoulder, said base having an extension arm;

a pressure plate slidingly mounted on said extension arm for juxtaposition on the humeral head of the shoulder;

a pivot arm having a first end and a second end, with said first end being hingedly mounted on said base for rotation of said pivot arm relative to said base and said second end being positioned for movement with said pressure plate;

a force indicator mounted on said pressure plate for measuring an applied force against said pressure plate; and a movement indicator mounted on said base for measuring rotation of said pivot arm in response to the applied force.

2. An apparatus as recited in claim 1 wherein said movement indicator is a Hall effect device.

3. An apparatus as recited in claim 1 further comprising a handle mounted on said extension arm, and wherein said pressure plate is slidingly mounted on said handle.

4. An apparatus as recited in claim 3 wherein said handle is slidingly mounted on said extension arm.

5. An apparatus as recited in claim 3 wherein said force indicator comprises a spring disposed between said handle and said pressure plate, and wherein the applied force is a function of compression of said spring between said handle and said pressure plate.

6. An apparatus as recited in claim 1 further comprising a computer means having a display mounted on said base, and wherein said computer means is connected with said force indicator to display the applied force and is connected with said movement indicator to display a rotation of said pivot arm.

7. An apparatus as recited in claim 1 further comprising a swivel plate mounted for rotation on said base for stationarily holding said base in juxtaposition on the clavicle.

8. An apparatus as recited in claim 1 further comprising a strap attached to said extension arm and engageable with the patient to hold said pressure plate against the shoulder during application of the applied force.

9. A device for measuring relative movement between bones of an anatomical joint which comprises:

an extension arm having a first end and a second end;

a base means attached to said first end of said extension arm for holding said first end substantially stationary relative to one bone of the joint;

a force indicator means attached to said second end of said extension arm and positioned against the other bone of the joint for measuring a force applied to the force indicator and against the other bone; and a movement indicator means mounted on said extension arm for sensing movement of said force indicator means in response to said applied force to obtain a measurement indicative of movement between the bones of the joint.

10. A device as recited in claim 9 wherein said force indicator means comprises:

a handle mounted on said extension arm;

a pressure plate slidingly mounted on said extension arm and juxtaposed on the humeral head of the arm; and a spring disposed between said handle and said pressure plate, and wherein the force is applied to said handle and the magnitude of the force is a function of compression of said spring between said handle and said pressure plate.

11. A device as recited in claim 10 wherein said movement indicator means comprises:

a pivot arm having a first end and a second end, with said first end being hingedly mounted on said base means for rotation of said pivot arm relative to said base means and said second end being positioned for free movement in response to movement of said pressure plate; and a hall effect device mounted on said base means for measuring rotational movement of said pivot arm to obtain said measurement indicative of movement between the bones of the joint.

12. A device as recited in claim 9 further comprising a computer means having a display mounted on said base means, and wherein said computer means is connected with said force indicator means to display the applied force and is connected with said movement indicator means to display said measurement of movement of said force indicator means.

13. A device as recited in claim 9 further comprising a strap attached to said extension arm and engageable with the joint to hold said force indicator against the said other bone during application of the applied force.

14. A device as recited in claim 9 further comprising a swivel plate mounted for rotation on said base means for stationarily holding said base means in juxtaposition with said one bone of the joint.

15. A method for using a device to evaluate the anatomical movement of a shoulder which comprises the steps of:

supporting the entire arm and the connecting shoulder area of a patient to establish a reactive force against the scapular spine;

positioning a base member of said device against the clavicle of the shoulder;

positioning a force application means of said device against the humeral head of the arm;

applying a force to the humeral head with said force application means;

measuring the force applied to the humeral head with a unit of said device which comprises a handle mounted on said force application means, a pressure plate sliding mounted on said handle, and a spring disposed between said handle and said pressure plate, wherein the applied force is a function of compression of said spring between said handle and said pressure plate; and measuring the movement of the humeral head relative to the clavicle with a pivot arm having a first end and a second end, said first end being hingedly mounted on said base member and a hall effect device is mounted on said base member to measure rotation of said pivot arm relative to said base member, said rotation being indicative of the anatomical movement of the shoulder.

16. A method as recited in claim 15 further comprising the step of providing a computer means having a display means mounted on said base, and wherein said computer means is connected with said force measuring unit to display the applied force, and with said movement measuring unit to display a rotation of said pivot arm.

17. A method as recited in 15 wherein said applying step is accomplished by pushing on said handle to generate the applied force.

* * * * *